(12) United States Patent
Latimer et al.

(10) Patent No.: US 6,610,903 B1
(45) Date of Patent: Aug. 26, 2003

(54) MATERIALS FOR FLUID MANAGEMENT IN PERSONAL CARE PRODUCTS

(75) Inventors: Margaret Gwyn Latimer, Alpharetta, GA (US); Gregory Marc Lefkowitz, Atlanta, GA (US); David Michael Matela, Alpharetta, GA (US); Jeffrey Michael Willis, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/433,487

(22) Filed: Nov. 4, 1999

Related U.S. Application Data

(60) Provisional application No. 60/112,902, filed on Dec. 18, 1998.

(51) Int. Cl.$^7$ .................................................. A61F 13/15
(52) U.S. Cl. .............................. 604/378; 604/385.101; 604/367
(58) Field of Search ................................. 604/367, 378, 604/384, 385.01, 385.101

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,005,957 A | 2/1977 | Savich | 425/80 |
| 4,100,324 A | 7/1978 | Anderson et al. | 428/288 |
| 4,340,563 A | 7/1982 | Appel et al. | 264/518 |
| 4,388,056 A | 6/1983 | Lee et al. | 425/83.1 |
| 4,592,708 A | 6/1986 | Feist et al. | 425/80.1 |
| 4,598,441 A | 7/1986 | Stemmler | 19/145 |
| 4,674,996 A | 6/1987 | Anno et al. | 474/110 |
| 4,761,258 A | 8/1988 | Enloe | 264/518 |
| 4,764,325 A | 8/1988 | Angstadt | 264/113 |
| 4,818,464 A | 4/1989 | Lau | 264/510 |
| 4,859,388 A | 8/1989 | Peterson et al. | 264/121 |
| 4,904,440 A | 2/1990 | Angstadt | 264/517 |

(List continued on next page.)

FOREIGN PATENT DOCUMENTS

| | | | |
|---|---|---|---|
| DE | 35 08 344 | 9/1986 | A61F/13/00 |
| EP | 0 391 814 | 10/1990 | D01D/5/253 |
| GB | 2 191 793 | 12/1987 | D01G/23/08 |
| WO | 90/12130 | 10/1990 | D01D/5/253 |
| WO | 92/11830 | 7/1992 | |
| WO | 93/02235 | 2/1993 | D01D/5/253 |
| WO | 98/07909 | 2/1998 | D01D/5/253 |

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

Primary Examiner—Weilun Lo
Assistant Examiner—Jacqueline F Stephens
(74) Attorney, Agent, or Firm—Steven D. Flack

(57) ABSTRACT

There is provided a fluid management material for personal care products which distributes artificial menses according to the gush/distribution test taught herein such that it has a distribution ratio of at least about 0.06. Its preferred that the fluid management material be part of an absorbent materials system having a first fibrous layer, a middle layer adjacent the first layer having hydrophilic oriented surface fibers, and a second fibrous layer adjacent the middle layer. In a personal care product configuration the oriented surface fibers result in a distribution ratio of at least 0.06 where the distribution ratio is a ratio of average of the mass of two end zones of a product divided by the mass of the center zone.

28 Claims, 5 Drawing Sheets

U.S. PATENT DOCUMENTS

| | | | |
|---|---|---|---|
| 4,908,175 A | 3/1990 | Angstadt | 264/113 |
| 5,004,579 A | 4/1991 | Wislinski et al. | 264/517 |
| 5,057,368 A | 10/1991 | Largman et al. | 428/397 |
| 5,069,970 A | 12/1991 | Largman et al. | 428/373 |
| 5,108,820 A | 4/1992 | Kaneko et al. | 428/198 |
| 5,108,827 A | 4/1992 | Gessner | 428/219 |
| 5,200,248 A | 4/1993 | Thompson et al. | 428/131 |
| 5,242,644 A | 9/1993 | Thompson et al. | 264/177.15 |
| 5,256,466 A | 10/1993 | Berringan et al. | |
| 5,268,229 A | 12/1993 | Phillips et al. | 428/400 |
| 5,277,976 A | 1/1994 | Hogle et al. | 428/397 |
| 5,302,446 A | 4/1994 | Horn | |
| 5,336,552 A | 8/1994 | Strack et al. | 428/224 |
| 5,356,405 A * | 10/1994 | Thompson et al. | 604/384 |
| 5,382,400 A | 1/1995 | Pike et al. | 264/168 |
| 5,458,963 A | 10/1995 | Meirowitz et al. | 428/297 |
| 5,466,410 A | 11/1995 | Hills | 264/172.11 |
| 5,466,513 A * | 11/1995 | Wanek et al. | 428/218 |
| 5,611,981 A | 3/1997 | Phillips et al. | 264/130 |
| 5,723,159 A | 3/1998 | Phillips et al. | 425/461 |
| 5,820,615 A | 10/1998 | Koczab | |
| 5,879,343 A * | 3/1999 | Dodge, II et al. | 604/378 |
| 5,883,231 A | 3/1999 | Achter et al. | 530/362 |
| 5,986,167 A * | 11/1999 | Arteman et al. | 604/380 |
| 6,060,638 A * | 5/2000 | Paul et al. | 604/378 |
| 6,103,376 A * | 8/2000 | Phillips et al. | 428/397 |
| 6,152,904 A * | 11/2000 | Matthews et al. | 604/378 |

* cited by examiner

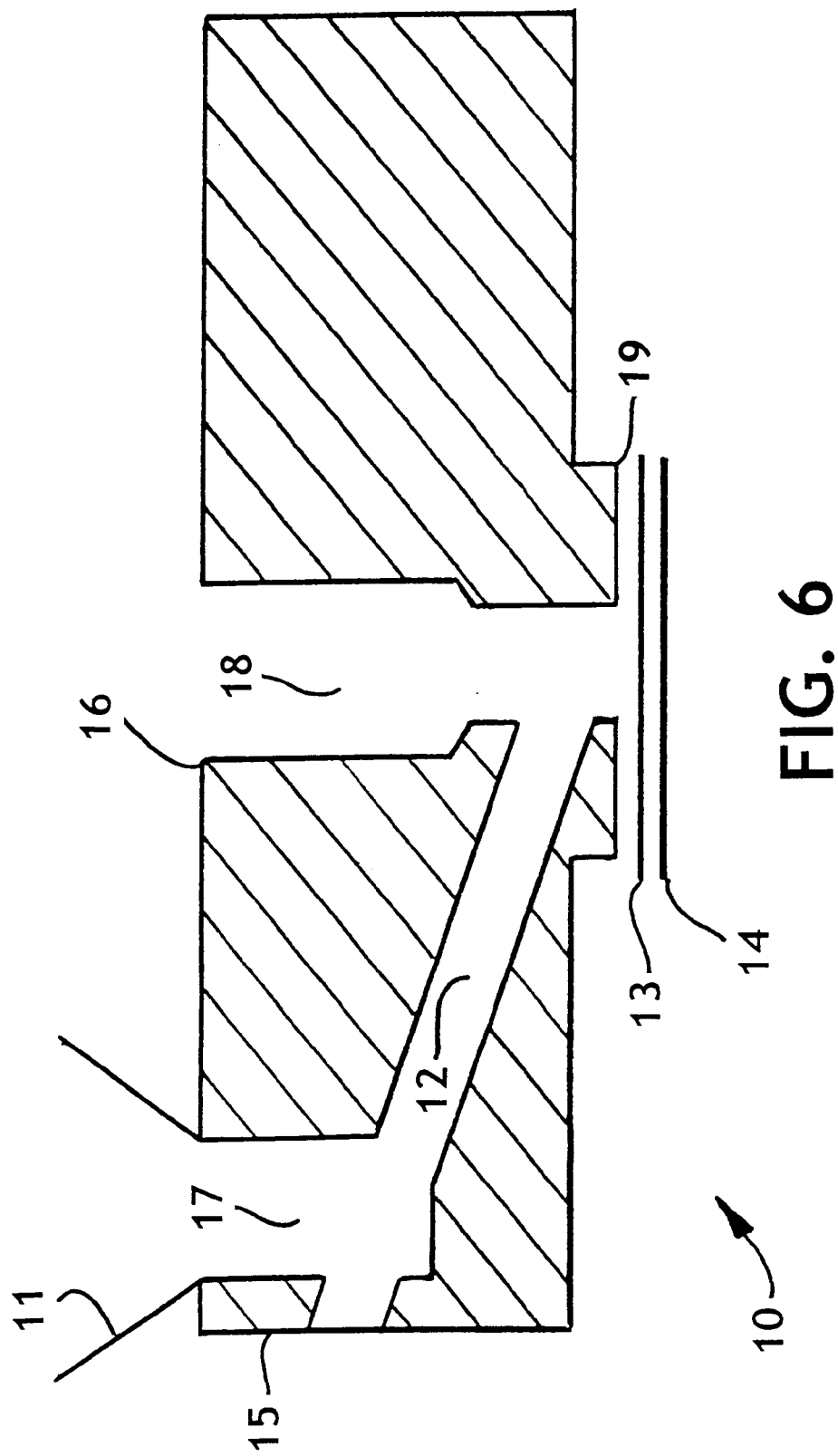

MATERIALS FOR FLUID MANAGEMENT IN PERSONAL CARE PRODUCTS

This Application claims priority from U.S. Provisional Application No. 60/112,902 filed Dec. 18, 1998.

FIELD OF THE INVENTION

The present invention relates to a structure in an article for personal care like diapers, training pants, absorbent underpants, adult incontinence products, bandages and feminine hygiene products, which can accept a surge of liquid.

BACKGROUND OF THE INVENTION

Personal care articles include such items as diapers, training pants, incontinence garments and devices, bandages and feminine hygiene products such as sanitary napkins, panty-liners and tampons and the like. The most basic design of all such articles typically includes a body side liner, an outercover and an absorbent core disposed between the body side liner and the outercover.

Feminine hygiene products like sanitary napkins, for example, have absorbent cores which have traditionally been designed to take in a thick, slow flowing fluid. Menstruating women, however, frequently complain of experiencing sudden gushes or surges of menstrual discharge which exits the body as a high volume, short delivery time, insult of fluid. An absorbent core designed to handle, slow moving flow usually has too small a pore structure to rapidly take in these gushes or limited surges of fluid and, as a result, fluid pooling or puddling on the product surface may result. Pooling on the surface can result in runoff or staining of the clothing and is unacceptable to the wearer. Alternatively, absorbent material(s) which have a sufficiently large pore structure to rapidly absorb gushes usually cannot redistribute that fluid to the extreme ends of the product, thus resulting in surge fluid accumulating in the center part of the pad where side leg pressure can cause leaks.

It is an object of this invention, therefore, to provide an absorbent structure which can rapidly take in sudden surges or gushes of fluid, pull the fluid away from the upper part of the absorbent to achieve a feeling of dryness for the user, redistribute that fluid along the entire length of the structure and release that fluid to other subsequent absorbent layers.

SUMMARY OF THE INVENTION

The objects of the invention are achieved by a fluid management material for personal care products which distributes artificial menses according to the gush/distribution test taught herein such that it has a distribution ratio of at least about 0.06.

Its preferred that the fluid management material be part of an absorbent materials system having a first fibrous layer, a middle layer adjacent the first layer having hydrophilic oriented surface fibers, and a second fibrous layer adjacent the middle layer. The density of the first layer is between about 0.02 and 0.14 g/cc. The density of the second layer is greater than the first layer and the second layer is preferably homogeneous in its resistance to liquid flow.

In a personal care product configuration the oriented surface fibers result in a distribution ratio of at least 0.06. It is preferred that products incorporating this invention have a minimum of 2.0 square meters of fiber surface area per product in the oriented surface fibers layer arranged in at least one zone of oriented surface fibers where the zone is at most 20 mm wide and the basis weight is at least 50 gsm.

BRIEF DESCRIPTION OF THE DRAWINGS

FIG. 6 is a rate block apparatus used in gush flow testing of materials.

DEFINITIONS

Figure 1:
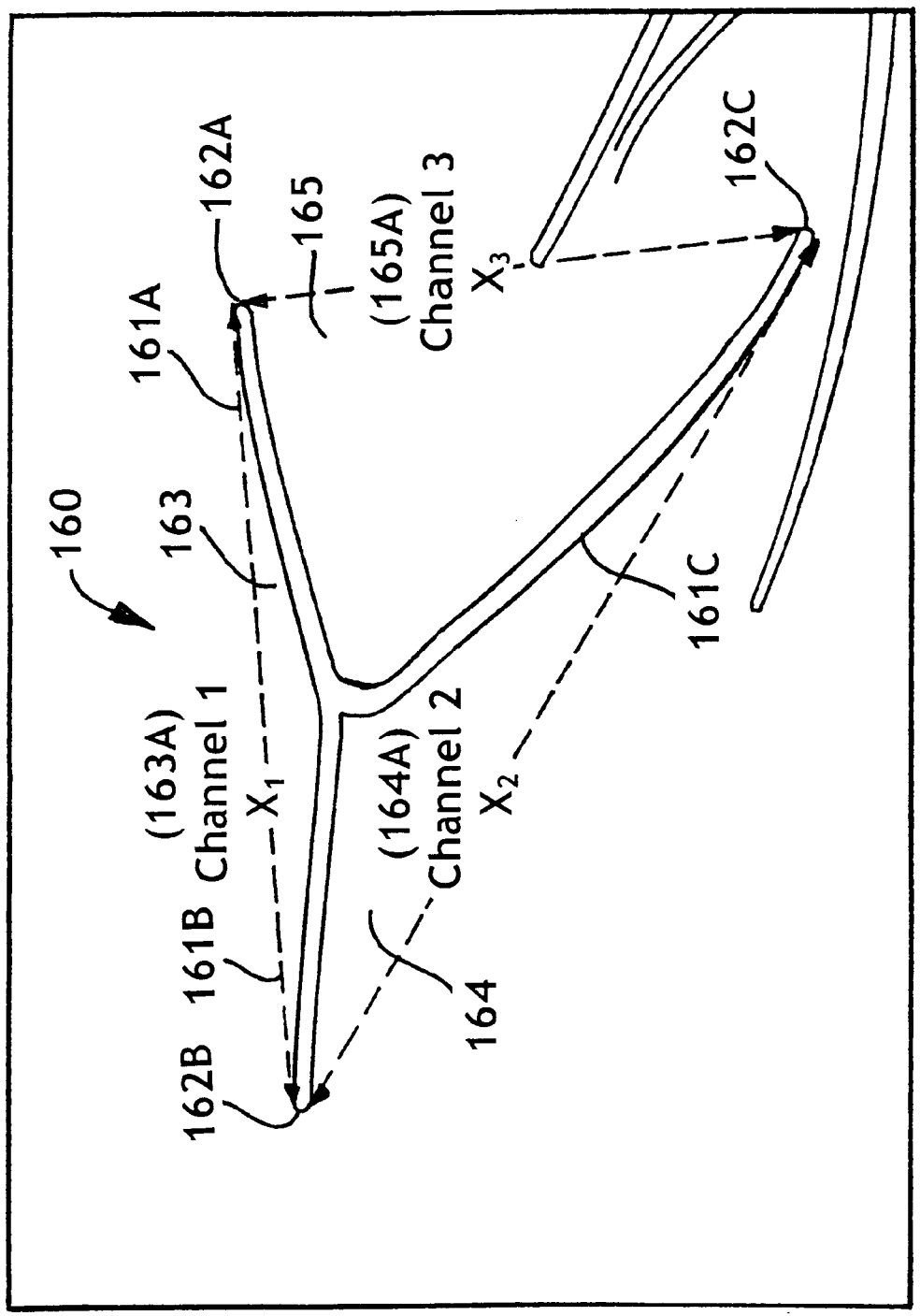
FIG. 1 shows a cross sectional view of a capillary surface material fiber suitable for use in the practice of this invention made according to WO 93/02235.

"Disposable" includes being disposed of after a single use and not intended to be washed and reused.

"Front" and "back" are used throughout this description to designate relationships relative to the garment itself, rather than to suggest any position the garment assumes when it is positioned on a wearer.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or "hydrophilic", while fibers having contact angles equal to or greater than to 90 ° are designated "nonwettable" or hydrophobic.

"Layer" when used in the singular can have the dual meaning of a single element or a plurality of elements.

"Liquid" means a non-particulate substance and/or material that flows and can assume the interior shape of a container into which it is poured or placed.

"Liquid communication" means that liquid is able to travel from one layer to another layer, or one location to another within a layer.

"Particles", in the context of this invention, refers to any geometric form such as, but not limited to, spherical grains, fibers or strands, flat surfaces or roughened surfaces, sheets, ribbons, strings, strands, or the like.

"Spray" and variations thereof include forcefully ejecting liquid, either as a stream or discrete elements, such as swirl filaments or atomized particles through an orifice, nozzle, or the like, by means of an applied pressure of air or other gas, by force of gravity, or by centrifugal force. The spray can be continuous or non-continuous.

"Conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. No. 5,277,976 to Hogle et al., and U.S. Pat. Nos. 5,069,970 and 5,057,368 to Largman et al., hereby incorporated by reference in their entirety, which describe fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Capillary Surface Materials" or CSMs are fibers or groups of such fibers which can spontaneously transport certain fluids on their surfaces. Fibers of this general type are discussed in, for example, PCT/US97/14607, WO 93/0223, WO 90/12130 and U.S. Pat. Nos. 5,268,229, 5,611,981 and 5,723,159. Likewise, "capillary channel fibers" offer improved fluid capacity and improved capability to transport and store fluid. Fibers of this general type are discussed in, for example, U.S. Pat. Nos. 5,200,248 and 5,242,644.

As used herein, the term "machine direction" or MD means the length of a fabric in the direction in which it is produced. The term "cross machine direction" or CD means the width of fabric, i.e. a direction generally perpendicular to the MD.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are microfibers and are generally continuous and have average diameters (from a sample of at least 10) larger than 7 microns, more particularly, between about 10 and 35 microns. The fibers may also have shapes such as those described in U.S. Pat. No. 5,277,976 to Hogle et al., U.S. Pat. No. 5,466,410 to Hills and 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

"Airlaying" is a well known process by which a fibrous nonwoven layer can be formed. In the airlaying process, bundles of small fibers having typical lengths ranging from about 3 to about 52 millimeters are separated and entrained in an air supply and then deposited onto a forming screen, usually with the assistance of a vacuum supply. The randomly deposited fibers then are bonded to one another using, for example, hot air or a spray adhesive. Airlaying is discussed in, for example, U.S. Pat. Nos. 4,005,957, 4,388, 056, 4,592,708, 4,598,441, 4,674,996, 4,761,258, 4,764,325, 4,904,440, 4,908,175, and 5,004,579, German Patent DE3508344 A1, European Patent Application 85300626.0 and British Patent Application 2,191,793.

As used herein, the term "coform" means a process in which at least one meltblown diehead is arranged near a chute through which other materials are added to the web while it is forming. Such other materials may be pulp, superabsorbent or other particles, natural polymer (for example, rayon or cotton) and/or synthetic polymer (for example, polypropylene, polyester, polyamide or acrylic) fibers, for example, where the fibers may have typical lengths ranging from about 3 to about 52 millimeters long. Coform processes are shown in commonly assigned U.S. Pat. No. 4,818,464 to Lau and U.S. Pat No. 4,100,324 to Anderson et al. Webs produced by the coform process are generally referred to as coform materials.

"Bonded carded web" refers to webs which are made from staple fibers where the typical fiber lengths range from about 19 to about 52 millimeters long. The fibers are sent through a combing or carding unit, which breaks apart and aligns the staple fibers in the machine direction to form a generally machine direction-oriented fibrous nonwoven web. The web is bonded by one or more of several known bonding methods.

Bonding of nonwoven webs may be achieved by a number of methods; powder bonding, wherein a powdered adhesive is distributed through the web and then activated, usually by heating the web and adhesive with hot air; pattern bonding, wherein heated calender rolls or ultrasonic bonding equipment are used to bond the fibers together, usually in a localized bond pattern, though the web can be bonded across its entire surface if so desired; through-air bonding, wherein air which is sufficiently hot to soften at least one component of the web is directed through the web; chemical bonding using, for example, latex adhesives which are deposited onto the web by, for example, spraying; and consolidation by mechanical methods such as needling and hydroentanglement.

"Personal care product" means diapers, training pants, absorbent underpants, adult incontinence products, feminine hygiene products and wound care products such as dressings and bandages.

"Feminine hygiene products" means sanitary napkins or pads and tampons.

"Target area" refers to the area or position on a personal care product where an insult is normally delivered by a wearer.

TEST METHODS AND MATERIALS

Material caliper (thickness) The caliper of a material is a measure of thickness and is measured at 0.05 psi with a Starret-type bulk tester, in units of millimeters.

Density The density of the materials is calculated by dividing the weight per unit area of a sample in grams per square meter (gsm) by the bulk of the sample in millimeters (mm) at 344.7 Pascals and multiplying the result by 0.001 to convert the value to grams per cubic centimeter (g/cc). A total of three samples would be evaluated and averaged for the density values.

Gush/distribution: This gush and distribution test attempts to simulate an absorbent material's ability to handle both continuous, slow flow as well as sudden, high volume gush flow. In addition, the test measures the effectiveness of an absorbent materials system to move fluid along its length.

Figure 4:
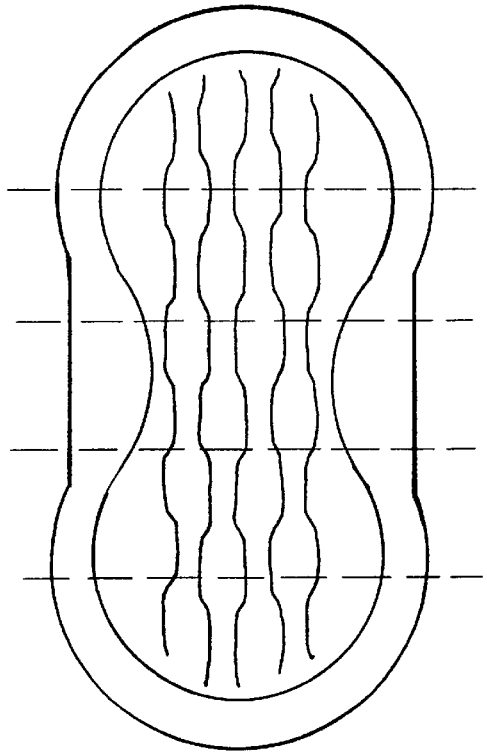
FIG. 4 shows a fluff pulp embossed with a longitudinal sine wave pattern and marked in 5 equal zones along its length.
Figure 5:
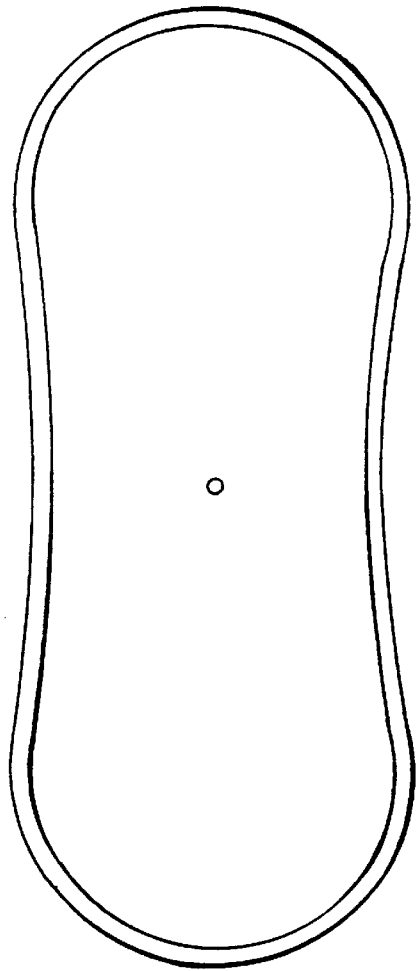
FIG. 5 shows an hourglass shape plate for use in the gush/distribution test.

A piece of the absorbent material or material system to be evaluated is cut 1.5 inches (38 mm) wide by 6 inches (152 mm) long and marked into 5 equal zones along its length. A desorbing fluff material used herein is cut into a rectangular piece measuring 3 inches (76 mm) wide by 6 inches (152 mm) long. The desorbing material used herein is a 600 gsm fluff s pulp (CR0054 from Coosa Mills of Coosa, Ala.), embossed with a longitudinal sine wave pattern as shown in FIG. 4. The desorbing fluff is also marked in 5 equal zones along its length. All materials should be weighed before starting the test. The 1.5 inch wide test sample is placed atop the desorbing material, centered uniformly across the width, matching longitudinal dimensions of each layer. A plate with an hourglass shape as shown in FIG. 5 (not to scale) is placed atop the test sample, matching its longest dimension with the longitudinal dimension of the materials. The hourglass plate is 8.25 inches (210 mm) long, 0.5 inches (13 mm) thick, 3.375 inches (86 mm) wide at each end lobe and 3 inches (76 mm) wide at the center, has a hole in the center with a diameter of 7 mm, weights about 240 grams and is preferably made from a plastic like, for example, PLEXI-GLAS® plastic, as it was herein.

The most difficult challenge for an absorbent material or materials system is to maintain its rapid fluid intake as readily when the absorbent has received some fluid as it did when the material was dry and unused. Testing gush intake time using a partially saturated absorbent system is a more challenging criterion than that established by testing a dry sample. This test procedure begins with a pre-saturating of the absorbent layers assembled. A continuous, slow flow of 5 ml of artificial menses is delivered to the absorbent sample. A syringe pump and a section of tubing are used to deliver artificial menses (prepared as taught below) to the hole in the center of the hourglass plate at a rate of 10 mls/hr for 30 minutes. The inventors used a 30 cc syringe (catalog no. 301626) from Becton Dickinson of New Jersey mounted on a Harvard PHD 200 multiple syringe programmable syringe pump (catalog no. 70-2002) from Harvard Apparatus, South Natick, Mass., though any equivalent delivery means would be suitable. A length of TYGON® flexible tubing measuring about 6 to 8" from Norton Performance Plastic Corporation located in Akron, Ohio, (catalog number AAB00006, 0.125" inner diameter, 0.1875 inch outer diameter, 0.03125" wall thickness) connects to one end of the syringe and its opposite end is inserted into the hole in the center of the hourglass plate in order to supply fluid to the absorbent system. If during the 30 minutes, the artificial menses overflows the hole in the hourglass plate, it should be absorbed with a paper towel of known weight. After 30 minutes, the addition of artificial menses is stopped and weights are recorded for the paper towel containing the overflow, the desorbing material and test sample.

The desorbing material and sample (without the hourglass plate) are reassembled into the same orientation as during the 30 minute fluid addition and are left undisturbed for 5 minutes. Next the system is insulted with a gush of fluid and its intake time is recorded. Referring to FIG. 6, a rate block as shown is placed in the center on top of the test material and its desorbing fluff assembly. The rate block 10 is 3 inches (76.2 mm) wide and 2.87 inches (72.9 mm) deep (into the page) and has an overall height of 1.125 inches (28.6 mm) which includes a center area 19 on the bottom of the rate block 10 that projects farther from the main body of the rate block 10 and has a height of 0.125 inches (3.2 mm) and a width of 0.886 inches (22.5 mm). The rate block 10 has a capillary 12 with an inside diameter of 0.186 inches (4.7 mm) that extends diagonally downward from one side 15 to the center line 16 at an angle of 21.8 degrees from the horizontal. The capillary 12 may be made by drilling the appropriately sized hole from the side 15 of the rate block 10 at the proper angle beginning at a point 0.726 inches (18.4 mm) above the bottom of the rate block 10; provided, however, that the starting point of the drill hole in the side 15 must be subsequently plugged so that test fluid will not escape there. The top hole 17 has a diameter of 0.312 inches (7.9 mm), and a depth of 0.625 inches (15.9 mm) so that it intersects the capillary 12. The top hole 17 is perpendicular to the top of the rate block 10 and is centered 0.28 inches (7.1 mm) from the side 15. The top hole 17 is the aperture into which the funnel 11 is placed. The center hole 18 is for the purpose of viewing the progression of the test fluid and is actually of an oval shape into the plane of FIG. 12. The center hole 18 is centered width-wise on the rate block 10 and has a bottom hole width of 0.315 inches (8 mm) and length of 1.50 inches (38.1 mm) from center to center of 0.315 inch (8 mm) diameter semi-circles making up the ends of the oval. The oval enlarges in size above 0.44 inches (11.2 mm) from the bottom of the rate block 10, for ease of viewing, to a width of 0.395 inches (10 mm) and a length of 1.930 inches (49 mm). The top hole 17 and center hole 18 may also be made by drilling.

A 2 ml gush of an artificial menses fluid as prepared below is delivered to the hole in the rate block using a micropipette and a timer or stopwatch is started. The timer is stopped when all the fluid is absorbed into the material or material system as observed through the chamber in the test apparatus. Remove the rate block and weigh the test sample and desorbing material to determine the fluid allocation between each layer. Cut the test sample and desorbing material along the marks, weighing each zone. A distribution ratio for each layer can then be calculated as the average of the mass of the two end zones divided by the mass of the center zone.

| A | B | C | D | E |
|---|---|---|---|---|

The distribution ratio can thus be seen to be:
(Fluid in Zone A+Fluid in Zone E)/2 divided by (Fluid in Zone C)

In order to meet the requirements of the instant invention, an absorbent materials system must provide an acceptable gush intake time as well as an acceptable distribution ratio.

The penetration time is the intake time required for a partially saturated absorbent materials system to absorb a sudden gush of 2 cc of liquid which has been deposited onto its uppermost surface. A small intake time, therefore, indicates that the materials system will readily accept fluid. The distribution ratio is a measure of how well a material system moves fluid along its length after the gush insult. The higher the distribution ratio, the better the material has distributed fluid along the product's length.

Artificial Menses Preparation: The artificial menses used was made from blood and egg white (according to U.S. Pat. No. 5,883,231) by separating the blood into plasma and red cells and separating the white into thick and thin portions. "Thick" means it has a viscosity after homogenization above about 20 centipoise at 150 $sec^{-1}$, combining the thick egg white with the plasma and thoroughly mixing, and finally adding the red cells and again thoroughly mixing. Blood, in this example defibrinated swine blood, was separated by centrifugation at 3000 rpm for 30 minutes, though other methods or speeds and times may be used if effective. The plasma was separated and stored separately, the buffy coat removed and discarded and the packed red blood cells stored separately as well. It should be noted that the blood must be treated in some manner so that it may be processed without coagulating. Various methods are known to those skilled in the art, such as defibrinating the blood to remove the clotting fibrous materials, the addition of anti-coagulant chemicals and others. The blood must be non-coagulating in order to be useful and any method which accomplishes this without damaging the plasma and red cells is acceptable.

Jumbo chicken eggs were separated, the yolk and chalazae discarded and the egg white retained. The egg white was separated into thick and thin portions by straining the white through a 1000 micron nylon mesh for about 3 minutes, and the thinner portion discarded. The thick portion of egg white which was retained on the mesh was collected and drawn into a 60 cc syringe which was then placed on a programmable syringe pump and homogenized by expelling and refilling the contents five times. The amount of homogenization was controlled by the syringe pump rate of about 100 ml/min, and the tubing inside diameter of about 0.12 inches. After homogenizing, the thick egg white had a viscosity of about 20 centipoise at 150 $sec^{-1}$ and was then placed in the centrifuge and spun to remove debris and air bubbles at about 3000 rpm for about 10 minutes After centrifuging, the thick, homogenized egg white, which contains ovamucin, was added to a 300 cc FENWAL® Transfer pack container using a syringe. Then 60 cc of the swine plasma was added to the FENWAL® Transfer pack container. The FENWAL® Transfer pack container was clamped, all air bubbles removed, and placed in a Stomacher lab blender where it was blended at normal (or medium) speed for about 2 minutes. The FENWAL® transfer pack container was then removed from the blender, 60 cc of swine red blood cells were added, and the contents mixed by hand kneading for about 2 minutes or until the contents appeared homogenous. A hematocrit of the final mixture showed a red blood cell content of about 30 weight percent and generally should be at least within a range of 28–32 weight percent for artificial menses made according to this example. The amount of egg white was about 40 weight percent.

The ingredients and equipment used in the preparation of artificial menses are readily available. Below is a listing of sources for the items used in the example, though of course other sources may be used providing they are approximately equivalent.

Blood (swine): Cocalico Biologicals, Inc., 449 Stevens Rd., Reamstown, Pa. 17567, (717) 336–1990.

Fenwal® Transfer pack container, 300 ml, with coupler, code 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242.

Hemata Stat-II device to measure hemocrits, serial no. 1194Z03127: Separation Technology, Inc., 1096 Rainer Drive, Altamont Springs, Fla. 32714.

DETAILED DESCRIPTION OF THE INVENTION

Personal care absorbent articles include such items as diapers, training pants, incontinence garments and devices, bandages, feminine hygiene products such as sanitary napkins, panty-liners and tampons, and the like. The most basic design of all such articles typically includes a body side liner, an outercover and an absorbent core disposed between the body side liner and the outercover.

Feminine hygiene products like sanitary napkins, for example, have absorbent cores which have traditionally been designed to take in a thick, slow flowing fluid. Menstruating women, however, frequently complain of experiencing sudden gushes or surges of menstrual discharge which exits the body as a high volume, short delivery time insult of fluid. An absorbent core designed to handle slow moving flow usually has too small a pore structure to rapidly take in these gushes or limited surges of fluid and, as a result, fluid pooling or puddling on the product surface may result. Pooling on the surface can result in runoff or staining of the clothing and is unacceptable to the wearer. Alternatively, absorbent materials which have a sufficiently large pore structure to rapidly absorb gushes usually cannot redistribute that fluid to the extreme ends of the product, thus resulting in surge fluid accumulating in the center part of the pad where side leg pressure can cause leaks.

What is needed and provided by this invention, is an absorbent structure which can rapidly take in sudden surges or gushes of fluid, pull the fluid away from the upper part of the absorbent to achieve a feeling of dryness for the user, redistribute that fluid along the entire length of the structure and optionally release that fluid to other subsequent absorbent layers. While this invention is primarily concerned with feminine hygiene products, the inventors believe the inventive material herein could function in the management of other bodily fluids like urine and will be especially effective for highly viscous fluids like BM (feces) and wound exudate and so be incorporated into diapers, training pants, incontinence garments and devices, bandages and the like.

A personal care product typically has a body side layer, optionally a fluid transfer layer, a fluid retention layer and a garment side layer. It may also have a distribution layer or other optional layers to provide specialized functions.

The body side layer is sometimes referred to as a body side liner or topsheet. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

The body side liner can be surface treated with a selected amount of surfactant, or otherwise processed to impart the desired level of wettability and hydrophilicity. If a surfactant is used, it can be an internal additive or applied to the layer by any conventional means, such as spraying, brush coating and the like, prior to the deposition of the next layer.

The garment side liner layer, also referred to as a backsheet or outer cover is the farthest layer from the wearer. The outer cover has traditionally been formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting or adjacent the personal care product. The outer cover may be embossed and/or matte finished to provide a more aesthetically pleasing appearance. Other alternative constructions for outer cover include woven or nonwoven fibrous webs that have been constructed or treated to impart the desired level, of liquid impermeability, or laminates formed of a woven or nonwoven fabric and thermoplastic film. The outer cover may optionally be composed of a vapor or gas permeable, microporous "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability. Backings may also serve the function of a mating member for mechanical fasteners, in the case, for example, where a nonwoven fabric is the outer surface.

The fluid retention layer or layers must absorb liquid from the adjacent body side layer in a controlled manner such that liquid may be stored away from contact with the body. This must occur even under gush conditions. A composite structure has been invented which can readily receive sudden gushes or surges of fluid, pull that fluid away from the body side liner, distribute the fluid along the length of the retention layer and pass the fluid to a bottom layer which will either function as the final fluid destination or function as a transfer area to move the fluid to another absorbent layer, which may be remote from the insult area.

The inventive composite structure preferably has at least three fibrous layers; a relatively low density upper or first fibrous layer adjacent to and in liquid communication with a middle layer or layers predominantly comprised of oriented surface fibers which are preferably substantially aligned which is in turn adjacent to and in liquid communication with a relatively higher density lower or second fibrous layer. The low density first layer is intended to provide good fluid intake of slow continuous fluid flow as well as sudden gush flow. By relatively lower density, what is meant is a density between about 0.02 and 0.14 g/cc. In the second fibrous layer, relatively higher density indicates a density above the density of the upper layer. The second fibrous layer desorbs the oriented surface fibers layer, regenerating void space within the middle layer and allowing the oriented fibers to continue to transport more fluid along the product length. The second fibrous layer with higher density is preferably homogeneous in its resistance to liquid flow, i.e., the lower layer must not contain areas of high and low resistance to liquid flow.

The upper and lower fibrous layers may be made from dominantly hydrophilic synthetic fibers, natural fibers and binders or a combination of such fibers, according to fibrous web making processes known to those skilled in the art including spunbonding, meltblowing, coforming, bonded carded web processes, airlaying and wet-laid including tissue formation. The upper and lower fibrous layers may be produced from the same or different nonwoven material formation methods.

The middle layer interposed between the low density first (or upper) layer and the higher density second (or lower) layer functions to desorb the upper layer, then distribute the fluid uniformly along the length of the product. The oriented surface fibers may be uniformly spread across the width of the layer. However the inventors have discovered that the most effective use of the fluid transporting capability of oriented surface fibers occurs when the fibers are aligned to the longitudinal direction of the product, and spaced into one or more tight clusters or bundles across the material width. These bundles reflect longitudinal zones or stripes of high levels of fiber basis weight and fibrous surface area and regions of small inter-fiber spacing for enhanced wicking distance and volume of fluid transported along the product length. The number of bundles and filament count per bundle will depend on the body fluid chemistry being transported and its volume present. More bundles and more filaments will be necessary for high fluid volume applications like diapers, incontinence products and training pants.

The oriented fiber surface layer or layers may be dominantly hydrophilic synthetic fibers, natural fibers and binders which may be in the form of staple or continuous filament round or shaped fibers, continuous filament capillary surface materials and fibers, continuous filament capillary channel materials and fibers, continuous filament superabsorbent fibers, stabilized staple fiber tows or slivers and other highly oriented hydrophilic nonwoven fiber webs such as bonded carded webs, oriented meltblown webs and neck stretched nonwoven webs, or a combination of such fibers, filaments and layers. Processes for making such layers include those for the production of the first and second fibrous layers. Oriented surface fibers may be mono-component fibers, biconstituent fibers and conjugate fibers.

The layer containing oriented surface fibers in the practice of the invention may include fibers of various deniers. The layer may have fibers of a single denier or a mixture of deniers and the range of deniers that will perform satisfactorily is believed by the inventors to be quite wide. Using a mixture of deniers in the layer may improve the wicking performance of the layer and may add to the structural stability of the layer as well.

In order to produce a successful personal care product using the instant invention, its believed that at least 2 square meters of surface area of oriented surface fibers is required. While this at first impression may seem like a large number for relatively small products such as feminine hygiene pads, there is a very large surface area per unit length. The oriented fibers should be placed in a product in a direction substantially aligned, i.e.; more than 75 percent of the hydrophilic fibers are aligned in the same direction, which is plus or minus 30° with the direction of fluid movement that is desired. The fibers may be placed in concentrated stripes or zones so that they are located near to each other to enhance wicking. These stripes or zones may each be up to 20 mm wide and should have a minimum basis weight of about 50 gsm. Multiple stripes or zones may be used in a product, depending on its size, the physical characteristics of the particular fluid to be handled as well as the volume of fluid to be handled.

Conjugate and biconstituent fibers provide the ability to stabilize the web via thermal bonding, for example. Upon thermal bonding, these fibers function as binder or adhesives, holding the other fibers in place to improve the integrity of the web. These fibers also aid in the transfer of liquid between layers. Such fibers may be used in any or all of the layers of a product.

Superabsorbent particles and fibers may also be used in the second fibrous layer in order to provide final fluid storage. It is important to note, however, that the amount of superabsorbent in a lower layer must be carefully considered since an excessive amount will overwhelm and significantly reduce the amount of wicking that occurs in the middle oriented surface fibers layer. An effective amount of superabsorbent, in whatever form, is that amount which allows wicking to continue.

Superabsorbents that are useful in the present inventions can be chosen from classes based on chemical structure as well as physical form. These include superabsorbents with low gel strength, high gel strength, surface cross-linked superabsorbents, uniformly cross-linked superabsorbents, or superabsorbents with varied cross-link density throughout the structure. Superabsorbents may be based on chemistries that include but are not limited to acrylic acid, iso-butylene/maleic anhydride, polyethylene oxide, carboxy-methyl cellulose, poly vinyl pyrrollidone, and poly vinyl alcohol. The superabsorbents may range in rate from slow to fast. The superabsorbents may be in the form of foams, macroporous or microporous particles or fibers, may have fuzzy or fibrous coatings or morphology. The superabsorbents may be in the shape of ribbons, particles, fibers, sheets or films. Superabsorbents may be in various length and diameter sizes and distributions. The superabsorbents may be in various degrees of neutralization. Neutralization occurs through use of counter ions such as Li, Na, K, Ca. Example of these types of superabsorbents may be obtained from Stockhausen, Inc. under the tradename FAVOR® 880. Examples of these types of superabsorbents obtained from Camelot are recognized as FIBERDRI® 1241 and FIBER-DRI® 1161. Examples of these types of superabsorbents obtained from Technical Absorbents, Ltd. are recognized as Oasis 101 and Oasis 111. Another Example included in these types of superabsorbents is obtained from Chemdall Inc. and is designated FLOSORB® 60 Lady. Another Example included in these types of superabsorbents is obtained from Sumitomo Seika of Japan and is recognized as SA60N® Type 2. Additional types of superabsorbents not listed here which are commonly available and known to those skilled in the art can also be useful in the present inventions.

The laminates of this invention may be made by producing each layer separately and thereafter bonding them together. Alternatively, it is also possible to produce such layers directly onto one another in a continuous in-line process. In either case, it is necessary to bond the layers together in some manner such that liquid communication between the layers is possible.

Such bonding may be done by, for example, through-air bonding, thermal bonding, adhesive bonding and the like as described above. The in-line process may allow simple heat bonding between the layers as they are produced, without any additional separate bonding steps. Any method for bonding layers such that liquid communication is permitted and which is known to those skilled in the art may be used.

The structures of this invention may be made from various materials including synthetic fibers, natural fibers, binders and oriented surface fibers.

Synthetic fibers include those made from polyamides, polyesters, rayon, polyolefins, acrylics, superabsorbents, Lyocel regenerated cellulose and any other suitable synthetic fibers known to those skilled in the art. Synthetic fibers may also include kosmotropes for product degradation.

Natural fibers include wool, cotton, flax, hemp and wood pulp. Pulps include standard soft-wood fluffing grade such as CR-1654 from Coosa Mills, high bulk additive formaldehyde free pulp (HBAFF) available from the Weyerhaeuser Corporation of Tacoma, Wash., and is a which is a crosslinked southern softwood pulp fiber with enhanced wet modulus, and a chemically cross-linked pulp fiber such as Weyerhaeuser NHB416. HBAFF has a chemical treatment which sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Acordis Fibers (formerly known as Courtaulds Fibers Incorporated) of Axis, Ala.

Binders include fiber, liquid or other binder means which may be thermally activated. Exemplary binders include conjugate fibers of polyolefins and/or polyamides, and liquid adhesives. Two such suitable binders are sheath core conjugate fibers available from KoSA Inc. (formerly Trevira Inc. and formerly Hoechst-Celanese), PO Box 4, Salisbury, N.C. 28145-0004 under the designation T-255 and T-256, though many suitable binder fibers are known to those skilled in the art, and are made by many manufacturers such as ES FiberVisions Inc. A suitable liquid binder is Kymene® 557LX binder available from Hercules Inc. of Wilmington, Del.

Oriented surface fibers like the preferred case capillary surface materials which can spontaneously transport certain fluids are discussed in, for example, PCT/US97/14607, (cognate of U.S. Pat. No. 6,103,376) European Patent Publication 0 391 814 A2, and U.S. Pat. Nos. 5,200,248, 5,242,644, 5,268,229, 5,611,981 and 5,723,159.

Figure 2:
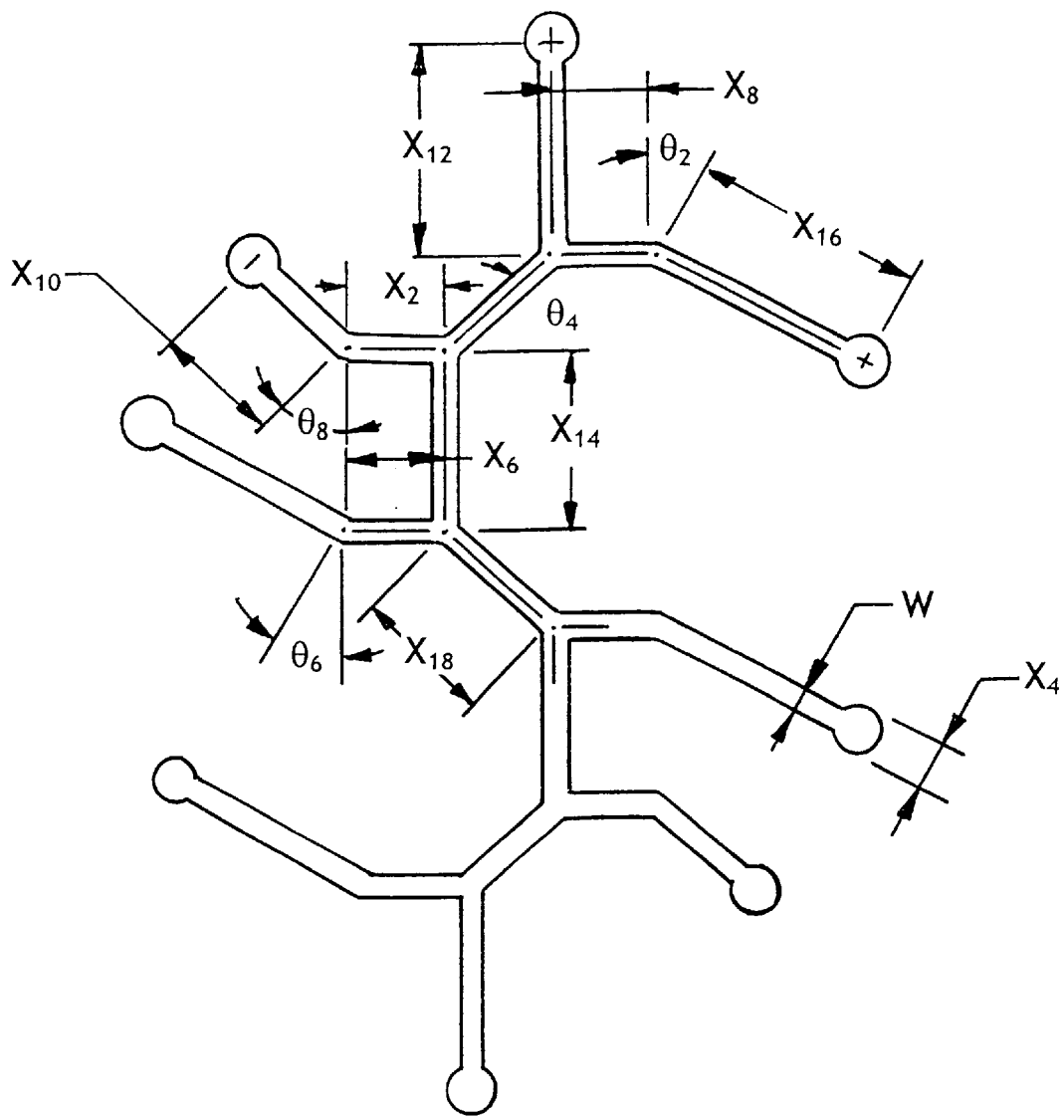
FIG. 2 shows a cross sectional view of a capillary surface material fiber suitable for use in the practice of this invention made according to PCT/US97/14607.

PCT/US97/14607 describes a bundle of fibers which comprises at least two fibers that when acting as individual fibers are poor transporters of fluids, yet when in a bundle the fibers provide a bundle that is an excellent transporter of fluids. The bundle has a Specific Volume greater than 4.0 cubic centimeters per gram (cc/gm), an average interfiber capillary width of from 25 to 400 microns, and a length greater than one centimeter (cm). At least one of the at least two fibers has a non-round cross section, a Single Fiber Bulk Factor greater than 4.0, a Specific Capillary Volume less than 2.0 cc/gm, and more than 70 percent of intrafiber channels having a capillary channel width greater than 300 microns. Preferably, the cross section defines a first arm having a length greater than 40 microns. The lengths of the cross section of the fibers range up to almost 1000 microns with some having arm lengths that are between 100 and 400 microns. Preferably the fibers have a denier between 15 and 250. FIG. 2 shows a fiber meeting the requirements of this patent application.

Figure 3:
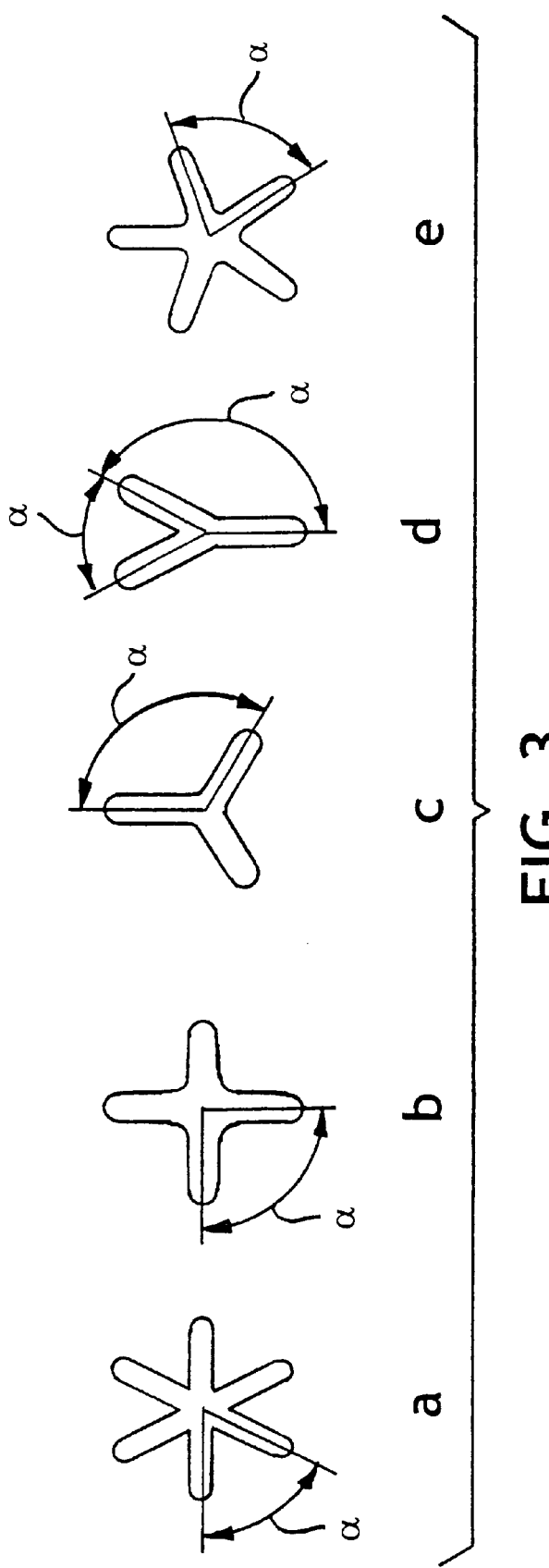
FIG. 3 shows other cross-sectional views of nonround fibers for use in the practice of this invention made according to U.S. Pat. 5,458,963.

European Patent Publication 0 391 814 A2 describes fibers which are capable of spontaneously transporting water on their surface. The fiber satisfies the equation:

$$(1-X \cos\theta_a)<0$$

wherein $\theta_a$ is the advancing contact angle of water measured on a flat film made from the same material as the fiber and having the same surface treatment, if any, X is a shape factor of the fiber cross section that satisfies the following equation:

$$X = \frac{Pw}{4r + (\pi - 2)D}$$

wherein Pw is the wetted perimeter of the fiber and r is the radius of the circumscribed circle circumscribing the fiber cross section and D is the minor axis dimension across the fiber cross section. FIG. 3 shows a fiber meeting the requirements of this patent application.

A number of examples of different materials satisfying the objective of the invention were made and are described in detail below. Note that Examples 2 and 7 are comparative and are not examples according to the invention.

EXAMPLE 1

The upper layer was an airlaid material made from 80 weight percent pulp and 20 weight percent binder fiber having a basis weight of about 75 gsm and a density of about 0.04 g/cc. The pulp was NB-416 made by Weyerhaeuser and the binder fiber was Type ES-C made by ES FiberVisions Inc. (formerly known as Danaklon of Varde, Denmark, Chisso Corp. of Japan, and/or Hercules Inc. of Wilmington, Del.).

The oriented surface fiber layer was made from shaped polyester fibers according to PCT/US97/14607 having greater than 100 filaments per pad and greater than 60 denier per filament.

The lower layer was an airlaid material made from 90 weight percent pulp and 10 weight percent binder fiber having a basis weight of about 75 gsm and a density of about 0.08 g/cc. The pulp was NB-416 made by Weyerhaeuser and the binder fiber was Type 255, 2.8 denier, made by KoSa Inc. of Charlotte, N.C.

EXAMPLE 2 (COMPARATIVE)

The upper layer was an airlaid material made from 80 weight percent pulp and 20 weight percent binder fiber having a basis weight of about 75 gsm and a density of about 0.04 g/cc. The pulp was NB-416 made by Weyerhaeuser and the binder fiber was Type ES-C made by ES FiberVisions Inc. There was no oriented surface fibers layer in this composite structure.

The lower layer was an airlaid material made from 90 weight percent pulp and 10 weight percent binder fiber having a basis weight of about 75 gsm and a density of about 0.08 g/cc. The pulp was NB-416 made by Weyerhaeuser and the binder fiber was Type 255, made by KoSa Inc. of Charlotte, N.C.

EXAMPLE 3

The upper layer was an airlaid material made from 40 weight percent pulp, 30 weight percent polyester fiber and 30 weight percent binder fiber having a basis weight of about 65 gsm and a density of about 0.04 g/cc. The pulp was NB-416 made by Weyerhaeuser, the sheath core conjugate binder fiber was Type 255, made by KoSa Inc. of Charlotte, N.C., and the polyester fiber was Type 295, 6 denier, also made by KoSa Inc.

The oriented surface fiber layer was made from shaped polyester fibers according to PCT/US97/14607 having greater than 100 filaments per pad and greater than 60 denier per filament.

The lower layer was an airlaid material made from 90 weight percent pulp and 10 weight percent binder fiber having a basis weight of about 75 gsm and a density of about 0.08 g/cc. The pulp was NB-416 made by Weyerhaeuser and the sheath core conjugate binder fiber was Type 255, made by KoSa Inc. of Charlotte, N.C.

EXAMPLE 4

The upper layer was a bonded carded web material made from 40 weight percent polyester fiber and 60 weight percent binder fiber having a basis weight of about 55 gsm and a density of about 0.025 g/cc. The polyester fiber was Type 295, 6 denier and the sheath core conjugate binder fiber was Type 255, both fibers made by KoSa Inc. of Charlotte, N.C.

The oriented surface fiber layer was made from shaped polyester fibers according to PCT/US97/14607 having greater than 100 filaments per pad and greater than 60 denier per filament.

The lower layer was an airlaid material made from 86 weight percent pulp and 14 weight percent binder fiber having a basis weight of about 80 gsm and a density of about 0.07 g/cc. The pulp was NB-416 made by Weyerhaeuser and the binder fiber was Type 255, made by KoSa Inc. of Charlotte, N.C.

EXAMPLE 5

The upper layer was an airlaid material made from 90 weight percent pulp and 10 weight percent binder fiber having a basis weight of about 65 gsm and a density of about 0.03 g/cc. The pulp was NB-416 made by Weyerhaeuser and the binder fiber was Type 255, made by KoSa Inc. of Charlotte, N.C.

The oriented surface fiber layer was made from shaped polyester fibers according to PCT/US97/14607 having greater than 100 filaments per pad and greater than 60 denier per filament.

The lower layer was a coformed material made from 50 weight percent pulp and 50 weight percent polypropylene microfiber meltblown fiber having a basis weight of about 75 gsm and a density of about 0.09 g/cc. The pulp was CF405 made by Weyerhaeuser and the polypropylene polymer was obtained under the tradename Montell PF-015 from Montell USA Inc. having offices in Wilmington, Del.

EXAMPLE 6

The upper layer was an airlaid material made from 80 weight percent pulp and 20 weight percent binder fiber having a basis weight of about 65 gsm and a density of about 0.04 g/cc. The pulp was NB-416 made by Weyerhaeuser and the binder fiber was Type ES-C made by ES FiberVisions Inc. The oriented surface fiber layer was made from round polyester fibers having greater than 100 filaments per pad and greater than 3 denier per filament.

The lower layer was an airlaid material made from 90 weight percent pulp and 10 weight percent binder fiber having a basis weight of about 75 gsm and a density of about 0.08 g/cc. The pulp was NB-416 made by Weyerhaeuser and the binder fiber was Type 255, made by KoSa Inc. of Charlotte, N.C.

EXAMPLE 7 (COMPARATIVE)

This single layer fabric was an airlaid material made from 90 weight percent pulp and 10 weight percent binder fiber having a basis weight of about 250 gsm and a density of about 0.14 g/cc. The pulp was NB-416 made by Weyerhaeuser and the binder fiber was Type 255, made by KoSa Inc. of Charlotte, N.C.

In all multilayer Examples the layers were bonded together by through-air thermal bonding in the order described. The materials of the Examples were tested according to the gush/distribution test and the results shown in Table 1.

TABLE 1

|  | Penetration Time (sec.) | Distribution Ratio |
|---|---|---|
| Example 1 | 10.98 | 0.238 |
| Example 2 | 15.00 | 0.006 |
| Example 3 | 15.06 | 0.184 |
| Example 4 | 9.99 | 0.183 |
| Example 5 | 14.94 | 0.189 |
| Example 6 | 18.65 | 0.118 |
| Example 7 | 27.60 | 0.001 |

As can be seen from these results, the composite structures of this invention absorb a gush insult quickly, especially when compared to (comparative) Example 7 as measured by the penetration time. Acceptable penetration times for personal care products should be less than 40 seconds. Distribution ratio results show that materials containing oriented surface fibers in a composite material move fluids along their length very well also, resulting in distribution ratios above 0.06 in all cases. This distribution ratio in combination with a penetration time under 40 seconds produces a products which delivers superior performance.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. An absorbent materials system for personal care products having a separate body side liner layer, said absorbent materials system comprising at least a three-layered fibrous laminate fabric comprising natural fibers and further including at least one internal layer, which fabric distributes artificial menses according to a gush/distribution test as given herein, resulting in a ratio of at least about 0.06, wherein said fabric comprises fibers which individually distribute fluid poorly and transport fluid well as a fiber bundle, and further wherein said fabric has a penetration time of less than 40 seconds.

2. The absorbent materials system of claim 1 wherein said fabric has at least 2 square meters of surface area of oriented surface fibers.

3. A personal care product comprising the fabric of claim 2 wherein said product has a width and a length.

4. The personal care product of claim 3 wherein said oriented surface fibers are substantially aligned.

5. The personal care product of claim 3 wherein said oriented surface fibers are aligned to the longitudinal direction of the product, in at least one-stripe, each of said at least one stripe being at most 20 mm wide along the product's width, and having a basis weight of at least 50 gsm.

6. The personal care product of claim 5, wherein the personal care product is a feminine hygiene pad.

7. The absorbent materials system of claim 1 wherein one of the laminate layers is a fibrous intake layer.

8. The absorbent materials system of claim 7 including a second fibrous layer, on a side of said internal layer opposite said fibrous intake layer, and having a higher density than said fibrous intake layer.

9. The absorbent materials system of claim 8 wherein said second layer is embossed.

10. The absorbent materials system of claim 8 wherein said second layer is embossed with a sine wave pattern.

11. The absorbent materials system of claim 10 wherein said layers are joined together with an adhesive binder.

12. The absorbent materials system of claim 8 wherein at least one layer is made according to a process selected from the group consisting of spunbonding, meltblowing, coforming, bonded carded web processes, airlaying and wet-laid formation.

13. A personal care product comprising the absorbent materials system of claim 8 wherein at least one layer is made from materials selected from the group consisting of cellulosic fibers, synthetic fibers and mixtures thereof.

14. A laminate comprising a first fibrous layer having a first density between about 0.02 and 0.14 g/cc, a middle layer adjacent to and in liquid communication with said first layer and comprising oriented fiber surface materials, and a second fibrous layer adjacent to and in liquid communication with said middle layer and having a density greater than said first density, and said middle layer comprises oriented surface fibers which individually distribute fluid poorly and transport fluid well as a fiber bundle, wherein said middle layer distributes artificial menses according to a gush/distribution test as given herein resulting in a ratio of at least about 0.06, and further wherein at least one of said first and said second fibrous layers comprises natural fibers.

15. The laminate of claim 14 wherein at least one layer is made according to a process selected from the group consisting of spunbonding, meltblowing, coforming, bonded carded web processes, airlaying and wet-laid tissue formation.

16. The laminate of claim 14 wherein said middle layer fibers are substantially aligned.

17. The laminate of claim 14 wherein said middle layer fibers are non-round.

18. The laminate of claim 14 further comprising superabsorbents.

19. The laminate of claim 14 further comprising conjugate fibers.

20. The laminate of claim 14 wherein said middle layer comprises superabsorbent fibers.

21. A personal care product comprising the laminate of claim 14.

22. The personal care product of claim 21 having at least 2 square meters of surface area of oriented surface fibers.

23. The personal care product of claim 22 wherein said oriented surface fibers are substantially aligned.

24. The personal care product of claim 22 wherein said oriented surface fibers are arranged in at least one zone, said at least one zone being at most 20 mm wide and having a basis weight of at least 50 gsm.

25. The personal care product of claim 21 wherein said second layer is embossed.

26. The personal care product of claim 25 wherein said second layer is embossed with a sine wave pattern.

27. The personal care product of claim 21 wherein said layers are joined together with an adhesive binder.

28. A feminine hygiene product with a liner layer, comprising:
- a first fibrous layer, adjacent said liner layer and having a density between about 0.02 and 0.14 g/cc, and;
- a middle layer adjacent to and in liquid communication with said first layer and comprising at least 2 square meters of surface area of substantially aligned, non-round, hydrophilic, oriented surface fibers, which individually distribute fluid poorly and transport fluid well as a fiber bundle, in at least one zone up to 20 mm wide and having a basis weight of about 50 gsm and;
- a second fibrous layer adjacent to and in liquid communication with said middle layer and having a density greater than said first layer,
- wherein said product has a penetration time of less than 40 seconds and wherein said product distributes artifical menses according to a gush/distribution test as given herein resulting in a distribution ratio of at least about 0.06, and further wherein at least one of said first or second fibrous layers comprises natural fibers.

* * * * *

UNITED STATES PATENT AND TRADEMARK OFFICE
CERTIFICATE OF CORRECTION

PATENT NO. : 6,610,903 B1
DATED : August 26, 2003
INVENTOR(S) : Margaret Gwyn Latimer et al.

Page 1 of 1

It is certified that error appears in the above-identified patent and that said Letters Patent is hereby corrected as shown below:

Column 6,
Line 36, "FIG. 12." should read -- FIG. 6. --

Signed and Sealed this

Sixteenth Day of November, 2004

JON W. DUDAS
*Director of the United States Patent and Trademark Office*